(12) United States Patent
Gupta et al.

(10) Patent No.: US 8,703,198 B2
(45) Date of Patent: Apr. 22, 2014

(54) WATER-BASED PERSONAL MOISTURIZERS AND LUBRICANTS, IN PARTICULAR VAGINAL LUBRICANTS, AND USES THEREOF

(75) Inventors: Vibha Gupta, Reading, MA (US); Boris Nikolic, Charlestown, MA (US); Vineet Gupta, Reading, MA (US)

(73) Assignee: Aquatrove Biosciences, Miami, FL (US)

( * ) Notice: Subject to any disclaimer, the term of this patent is extended or adjusted under 35 U.S.C. 154(b) by 962 days.

(21) Appl. No.: 11/364,200

(22) Filed: Mar. 1, 2006

(65) Prior Publication Data

US 2006/0204557 A1 Sep. 14, 2006

Related U.S. Application Data

(60) Provisional application No. 60/657,440, filed on Mar. 2, 2005.

(51) Int. Cl.
*A61K 9/70* (2006.01)

(52) U.S. Cl.
USPC .......................................................... 424/488

(58) Field of Classification Search
CPC .................................................. A61K 9/0034
USPC .......................................................... 424/488
See application file for complete search history.

(56) References Cited

U.S. PATENT DOCUMENTS

| | | | |
|---|---|---|---|
| 3,719,594 A * | 3/1973 | Borochaner | .................. 210/190 |
| 3,965,906 A | 6/1976 | Karami | |
| 3,965,908 A | 6/1976 | Posthuma et al. | |
| 4,039,662 A | 8/1977 | Hecht et al. | |
| 4,120,949 A | 10/1978 | Bapatla et al. | |
| 4,128,631 A | 12/1978 | Lundmark et al. | |
| 4,184,974 A | 1/1980 | Van Leuven | |
| 4,232,003 A | 11/1980 | Posthuma et al. | |
| 4,267,268 A | 5/1981 | Nelson, Jr. | |
| 4,527,988 A | 7/1985 | Lutz et al. | |
| 4,670,256 A | 6/1987 | Doran | |
| 4,795,761 A | 1/1989 | Curtis-Prior et al. | |
| 4,883,658 A | 11/1989 | Holly | |
| 4,923,699 A * | 5/1990 | Kaufman | ...................... 424/427 |
| 4,981,686 A | 1/1991 | Hardy | |
| 5,013,714 A | 5/1991 | Lindstrom et al. | |
| 5,015,474 A | 5/1991 | Parnell | |
| 5,102,783 A | 4/1992 | Alkemade et al. | |
| 5,128,132 A | 7/1992 | Parnell | |
| 5,208,031 A | 5/1993 | Kelly | |
| 5,209,927 A * | 5/1993 | Gressel et al. | ............. 424/78.04 |
| 5,342,617 A | 8/1994 | Gold | |
| 5,366,964 A | 11/1994 | Lindstrom et al. | |
| 5,389,657 A | 2/1995 | Madsen | |
| 5,424,078 A * | 6/1995 | Dziabo et al. | .................. 424/661 |
| 5,512,289 A | 4/1996 | Tseng et al. | |
| 5,545,673 A | 8/1996 | Kelly | |
| 5,577,514 A | 11/1996 | Zimmerman | |
| 5,591,426 A | 1/1997 | Dabrowski et al. | |
| 5,592,949 A | 1/1997 | Moench et al. | |
| 5,617,877 A | 4/1997 | Moench et al. | |
| 5,800,807 A | 9/1998 | Hu et al. | |
| 5,857,959 A | 1/1999 | La Vean et al. | |
| 5,879,877 A | 3/1999 | Ellington et al. | |
| 5,885,591 A | 3/1999 | Ahmad et al. | |
| 5,895,645 A | 4/1999 | Dabrowski et al. | |
| 5,897,987 A | 4/1999 | Oliver et al. | |
| 5,899,848 A | 5/1999 | Haubrich | |
| 5,902,593 A | 5/1999 | Kent et al. | |
| 5,980,477 A * | 11/1999 | Kelly | ............................... 602/77 |
| 6,139,848 A | 10/2000 | Ahmad et al. | |
| 6,140,121 A | 10/2000 | Ellington et al. | |
| 6,171,778 B1 | 1/2001 | Ellington et al. | |
| 6,231,849 B1 | 5/2001 | Schiller | |
| 6,280,716 B1 | 8/2001 | Ratcliff | |
| 6,281,251 B1 | 8/2001 | Digenis et al. | |
| 6,321,750 B1 | 11/2001 | Kelly | |
| 6,365,200 B1 | 4/2002 | Birnholz et al. | |
| 6,368,786 B1 | 4/2002 | Saint-Ramon et al. | |
| 6,428,791 B1 | 8/2002 | Lezdey et al. | |
| 6,585,987 B1 | 7/2003 | Fransoni | |
| 6,593,138 B1 | 7/2003 | Oliver et al. | |
| 6,593,309 B2 | 7/2003 | Ellington et al. | |
| 6,610,331 B1 | 8/2003 | Sweazy et al. | |
| 6,620,797 B2 * | 9/2003 | Chowhan et al. | ................ 514/57 |
| 6,737,084 B2 | 5/2004 | Crosby et al. | |
| 6,861,079 B2 | 3/2005 | Sweazy et al. | |
| 6,864,046 B1 | 3/2005 | Prien et al. | |
| 2002/0193350 A1 | 12/2002 | Ellington et al. | |
| 2003/0176479 A1 * | 9/2003 | Cameron et al. | ............... 514/381 |
| 2003/0224070 A1 | 12/2003 | Sweazy et al. | |
| 2004/0009223 A1 * | 1/2004 | Garg et al. | ..................... 424/484 |

(Continued)

FOREIGN PATENT DOCUMENTS

| | | | | |
|---|---|---|---|---|
| EP | 0818194 | * | 1/1998 | ............... A61K 9/08 |
| EP | 0888117 | | 8/2002 | |
| WO | WO-91/06283 | | 5/1991 | |
| WO | WO-98/43614 | | 10/1998 | |

OTHER PUBLICATIONS

U.S. Appl. No. 12/281, 295, filed Aug. 29, 2008, Gupta et al.

(Continued)

*Primary Examiner* — Jake Vu

(74) *Attorney, Agent, or Firm* — Duane Morris LLP; Lee Crews

(57) ABSTRACT

There is a need for water-based sperm- and egg-friendly vaginal lubricant. We describe novel water-based nature-friendly personal moisturizers and lubricants that relive vaginal dryness. In addition to being non-spermicidal, sperm- and egg-friendly and biological-fluids mimicking, these personal moisturizers and lubricants also enhance sperm survival and motility, promote binding of sperm to eggs and facilitate the process of fertilization. Novel articles, and systems as well as methods of preparation and use of the novel compositions are also provided.

12 Claims, No Drawings

(56) References Cited

U.S. PATENT DOCUMENTS

| | | | |
|---|---|---|---|
| 2004/0073964 A1 | 4/2004 | Ellington et al. | |
| 2004/0102429 A1* | 5/2004 | Modak et al. | 514/184 |
| 2005/0076917 A1 | 4/2005 | Wray et al. | |

OTHER PUBLICATIONS

Agarwal et al., Effect of Vaginal Lubricants in Sperm Motility and Chromatin Integrity: a Prospective Comparative Study, Fertility and Sterility, 89:375-379 (2008).

Aitken, R.J., "Sperm Function Tests and Fertility," Int. J. Androl., 29(1):69-75, discussion 105-108 (2006).

Anderson et al., "The Effects of Coital Lubricants on Sperm Motility in vitro," Hum. Reprod. 13(12):3351-3356 (1998).

Borland et al., "The Elemental Composition of the Environments of the Gametes and Preimplantation Embryo During the Initiation of Pregnancy," Biol. Reprod., 16(2):147-157 (1977).

Butler, D., "The Fertility Riddle," Nature, 432(7013):38-39 (2004).

Champion et al., "Playing for Half the Deck: the Molecular Biology of Meiosis," Nat. Cell. Biol., October, 4 supplement S50-S56 (2002).

Charo, R.A., " Children by Choice: Reproductive Technologies and the Boundaries of Personal Autonomy," Nat. Cell. Biol., Oct., 4 supplement S23-S28 (2002).

Chen et al., "Soluble Adenylyl Cyclase as an Evolutionarily Conserved Bicarbonate Sensor," Science, 289(5479):625-628 (2000).

Eisenbach et al., "Sperm Guidance in Mammals-an Unpaved Road to the Egg," Nature, 7:276-285 (2006).

Evans et al., "The State of the Union: the Cell Biology of Fertilization," Nat. Cell. Biol., October, 4 supplement S57-S63 (2002).

Fraser, L.R., "ART: Boon or Bane," Nat. Cell. Biol., October, 4 supplement S10-S13 (2002).

Frishman et al., "Evaluation of Astroglide, a New Vaginal Lubricant: Effects of Length of Exposure and Concentration on Sperm Mobility," Fertil. Steril. 58(3):630-632 (1992).

Garg et al., "Compendium of Pharmaceutical Excipients for Vaginal Formulations," Pharm. Tech, Drug Delivery (2001).

Glander et al., "Binding of Annexin V to Plasma Membranes of Human Spermatozoa: a Repid Assay for Detection of Membrane Changes After Cryostorage," Mol. Hum. Reprod., 5(2):109-115 (1999).

Glasier, A., "Contraception—Past and Future," Nat. Cell. Biol., October, 4 supplement S3-S6 (2002).

Goldenberg et al., "The Effect of Vaginal Lubricants on Sperm Motility in vitro," Fertil. Steril., 26(9): 872-873 (1975).

Greaves et al., "A Fertile Field," Nat. Cell. Biol., October, 4 supplement S2 (2002).

International Search Report Application U.S. Appl. No. PCT/US2007/005407 Mailed Feb. 10, 2007.

Katz et al., "The Economic Impact of the Assisted Reproductive Technologies," Nat. Cell. Biol., October, 4 supplement S29-S32 (2002).

Kirichok et al., "Whole-Cell Patch-Clamp Measurements of Spermatozoa Reveal an Alkaline-Activated Ca2+ Channel," Nature, 439(7077): 737-740 (2006).

Kutteh et al., "Vaginal Lubricants for the Infertile Couple: Effect on Sperm Activity," Int. J. Fertil. Menopausal Stud., 41(4):400-404, (1996).

Limone et al., "The Effect of Artificial Vagina Lubricants on Stallion Sperm Motion Measures and Semen pH During Cooled Storage," Theriogenology, 58:333-336 (2002).

Matzuk et al., "Genetic Dissection of Mammalian Fertility Pathways," Nat. Cell. Biol., October, 4 supplement S41-S49 (2002).

Press Release from Aurora Pharmaceuticals Pty. Ltd., [online], [retrieved on Apr. 24, 2005] Retrieved from <URL: http://www.aurorapharm.com/press_release_astroglide.html>.

Powell, K., "Fertility Treatments: Seeds of Doubt," Nature, 422(6933): 656-658, (2003).

Powell, K., "Skeptics Demand Duplication of Controversial Fertility Claim," 11(9):911 (2005).

Primakoff, P., "Penetration, Adhesion, and Fusion in Mammalian Sperm-Egg Interaction," Science, 296(5576):2183-2185 (2002).

Rosatto et al., "Role of Seminal Osmolarity in the Regulation of Human Sperm Motility," Int. J. And., 25:230-235 (2002).

Schatten, G.P., "Safeguarding ART," Nat. Cell. Biol., October, 4 supplement S19-S22 (2002).

Studies on INGfertility Technology Presented at Major Medical Meetings, [online], [Retrieved on Jun. 7, 2009] Retrieved from <URL: http://www.preseed.com/TheScience/Medical_Meetings.php>.

Sharpe et al., "Environment, Lifestyle and Infertility—an Intergenerational Issue," Nat. Cell. Biol., October, 4 supplement S33-S40 (2002).

Tagatz et al., "The Effect of Vaginal Lubricants on Sperm Motility and Viability in vitro," Am. J. Obstet. Gynecol., 113(1): 88-90 (1972).

Turner, R.M., "Tales from the Tail: What do We Really Know About Sperm Motility?," J. Andrology, 24(6): 790-803 (2003).

Visconti et al., "Novel Signaling Pathways Involved in Sperm Acquisition of Fertilizing Capacity," Journ. Rep. Imm. 53:133-150 (2002).

Wassarman, P.M., "Channels of Communication in the Ovary," Nat. Cell. Biol., October, 4 supplement S7-S9 (2002).

Winston et al., "Are We Ignoring Potential Dangers of in vitro Fertilization and Related Treatments," Nat. Cell. Biol., October, 4 supplement S14-S18 (2002).

510(k) Summary Pre' Vaginal Lubricant, No. K051436, May 18, 2005.

Restored Balance—Vaginal Moisturizing Gel, Simplee Wonderful Vaginal Moisturizing Gel, © 2006, [online], [retrieved on May 9, 2007] Retrieved from <URL: http://www.restoredbalanceonline.com/vmg.htm>.

Sylk Sexual Lubricant—Vaginal Dryness Lubricant, [online], [retrieved on May 9, 2007] Retrieved from <URL: http://sylkonline.com/index.html>.

Sylk Personal Lubricant—Sylk Sexual Enhancement FAQ's, SYLK Frequently Asked Questions, [online], [retrieved on May 9, 2007] Retrieved from <URL: http://sylkonline.com/sylkpersonal-lubricantfaq.html>.

Wal-Med, Inc., About Fem*Glide*™, revised Mar. 2007, [online], [retrieved on May 9, 2007] Retrieved from <URL: http://www.wallace-medical.com/femglide.htm>.

Wal-Med, Inc., Slippery_Stuff®, revised Mar. 2007, [online], [retrieved on May 9, 2007] Retrieved from <URL: http://www.wallace-medical.com/slipstuf.htm>.

* cited by examiner

WATER-BASED PERSONAL MOISTURIZERS AND LUBRICANTS, IN PARTICULAR VAGINAL LUBRICANTS, AND USES THEREOF

CROSS-REFERENCE TO RELATED APPLICATIONS

This application claims the benefit of U.S. Provisional Application No. 60/657,440, filed Mar. 2, 2005, the disclosure of which is hereby incorporated by reference herein.

STATEMENT REGARDING FEDERALLY SPONSORED RESEARCH OR DEVELOPMENT

None.

TECHNICAL FIELD

The present invention relates generally to novel compositions for promoting in vivo and in vitro survival, improved function of sperm, oocyte, embryo, cell and tissue and increased fertilization potential of sperm and oocyte. These compositions are especially useful as human and other animal tissue lubricants and moisturizers, in particular as non-spermicidal vaginal lubricants, and for mimicking natural fluids. This invention also relates to systems, articles and methods of preparation and use of the novel aqueous compositions.

BACKGROUND OF THE INVENTION

Naturally lubricating physiological fluid or mucus is normally present in the vagina and the lack of sufficient vaginal lubrication causes vaginal tissue to become dry and irritated and may cause discomfort, pain and sometimes bleeding. There are a number of causes for this condition (reviewed elsewhere). In couples trying to conceive (TTC), vaginal dryness issues further complicate the process of coitus and fertilization. Stress and delay in conceiving, due to the recent worldwide shift in timing of marriage and conception, further complicates the vaginal dryness issue.

In nature, spermatozoa are in a milieu that has a pH of around 7.8-8.2, whereas the pH in the vagina is around 4.5 (which favors normal vaginal flora but is harmful to sperm). Free-swimming sperm approach eggs within the oviduct in order to initiate fertilization. Prior to entering the female tract, the sperm are stored within the cauda epididymis in a functionally inactive state, immotile and incapable of interacting with eggs (1-16). The cauda epididymis stored sperm are kept viable by the presence of ions, energy substrates, and nutrients in a pH and tonically balanced solution of the milieu. A series of biochemical steps, aided by the biological milieu, transforms the inactive sperm into free-swimming and functional cells that are capable of fertilization with eggs. For example, sperm capacitation involves, among other things, cholesterol efflux from sperm membranes, cAMP-dependent signaling (which requires extracellular bicarbonate ions, among other agents), and the elevation of intracellular pH and bicarbonate levels with the associated stimulation of cAMP production (which is linked to the control of flagellar motility, among other things). Additionally, among other things, progesterone may also regulate some aspects of capacitation. Lower than physiological levels of potassium ions also favor capacitation (23). Capacitated sperm penetrate the cumulus oophorus assisted by, among other things, a cell surface hyaluronidase, contact the zona pellucida and undergo a acrosome reaction (which is calcium-dependent, among other things). Sperm adhesion to the zona pellucida is based on, among other things, binding between cell surface receptors and ligands on the cells (such as integrins) and on protein-carbohydrate recognition processes through the association. After completion of the acrosome reaction, sperm penetrate the zona pellucida, subsequently contacting and fusing with the plasma membrane of the egg, leading to fertilization. Furthermore, the motility of the sperm during this process is also an energy intensive process, and is aided by energy substrates, including pyruvate, lactate and glucose. Most of these findings have been corroborated by various in vitro culture studies with sperm. However, what has not been obvious so far is our finding that inclusion of such agents in lubricant compositions improves the viability, motility and fertilization potential of the sperm that come in contact with lubricants and moisturizers. A composition that improves viability, motility and/or mucus penetration of sperm after transfer to a female should greatly improve the chances of fertilization. Such novel compositions are also non-toxic to the oocyte and the fertilized embryo. The novel compositions of this invention are particularly useful as lubricants for use prior to or during coitus. An object of this invention is to provide systems, articles, and methods of manufacture and use of such novel compositions to facilitate fertilization.

A number of different lubricant compositions and methods of use are known in the art. However, most over-the-counter (OTC) lubricants that are currently available reduce sperm viability or motility or both (18-22). Also, they prevent contact between sperm and egg. Commonly available lubricants, such as K-Y Jelly and Vaseline, are not ideal due to their poor water solubility, poor consistency, and above all, because they are spermicidal (18-22). Thus, they harm sperm and oocyte, decrease sperm motility as well as prevent binding of sperm with egg and thereby hinder the process of fertilization. Additionally, none of these compositions contain cell viability maintaining agents or fertilization and other function enhancing agents. U.S. Pat. Nos. 3,965,906 and 4,883,658 generally describe the use of an aqueous solution of a high molecular weight polyacrylamide as vaginal lubricant. U.S. Pat. Nos. 3,965,906 and 4,883,658 do not disclose cell viability maintaining agents or fertilization and other function enhancing agents. U.S. Pat. No. 4,128,631 generally discloses a lubricant composition that includes a high molecular weight acrylamide-based polymer. U.S. Pat. No. 4,128,631 also does not disclose cell viability maintaining agents or fertilization and other function enhancing agents. U.S. Pat. No. 4,670,256 is directed toward methods for temporarily conditioning a vaginal tract to become non-acidic through the use of an alkalizer. U.S. Pat. No. 4,670,256 also does not disclose cell viability maintaining agents or fertilization and other function enhancing agents. U.S. Pat. No. 5,885,591 generally describes spermicidal lubricant containing glycerin, polyhydric alcohols and preservative. U.S. Pat. No. 5,885,591 is toxic to sperm and does not disclose cell viability maintaining agents or fertilization and other function enhancing agents. U.S. Pat. No. 6,139,848 generally describes personal lubricant containing at least one water soluble polyhydric alcohol, a water soluble polymer derived from cellulose, tocopherol or a tocopherol derivative, an emulsifier and water. U.S. Pat. No. 6,139,848 also does not disclose cell viability maintaining agents or fertilization and other function enhancing agents. U.S. Pat. No. 5,342,617 generally describes an aqueous lubricant containing high molecular weight polyethyl oxide, a humectant polyol, and a sterilizing agent. U.S. Pat. No. 5,342,617 also does not disclose cell viability maintaining agents or fertilization and other function enhancing agents. U.S. Pat. No. 6,428,791 describes lubricants that contain plant or herb agents in an aqueous lubricant to generate heat, enhance blood circulation, and increase nitrous oxide levels at the site of administration. U.S. Pat. No. 6,428,791 also does not disclose cell viability maintaining agents or fertilization and other function enhancing agents. Thus, even though some of the above-mentioned disclosures describe aqueous compositions, they do not disclose viability maintaining agents or fertilization and other function enhancing agents—that are essential for maintaining viability of sperm and oocyte, as described above. Additionally, sperm motility is hindered in such viscous solutions. U.S. Pat. No. 4,184,974 generally discloses lubricant compositions that include polypectate aqueous solutions containing detergents and silver ions as topical biocidal agent. U.S. Pat. No. 4,184,974 does not disclose cell viability maintaining agents or fertilization and other function enhancing agents. Additionally, the described compositions are spermicidal due to the presence of detergents and other biocidal agents. U.S. Pat. Nos. 5,015,474 and 5,128,132 generally describe the use of oil extracted from the Yerba Santa plant to treat mild to severe dryness of dermal and mucosal membranes. U.S. Pat. Nos. 5,015,474 and 5,128,132 also do not disclose cell viability maintaining agents or fertilization and other function enhancing agents. Additionally the U.S. Pat. Nos. 5,015,474 and 5,128,132 compositions are non-aqueous and thus incompatible with healthy sperm and oocyte, which prefer an aqueous environment. Sperm motility may also be compromised in these compositions.

One of the requirements for a lubricant to be useful in helping with the process of fertilization is that it not reduce the viability of the cells involved in this process. A second important requirement is that the compositions not negatively impact the motility, penetration and/or fertilization potential of sperm as well as fertilization potential of oocyte. Finally, the compositions should also not harm the oocyte or the fertilized embryo. And even though there are a few non-spermicidal lubricants known in the art, the current compositions do not fulfill all of the above-described objectives. More specifically, certain compositions also are known to comprise components that compromise cell viability, motility and/or other reproductive cell function. Thus, the lubricous compositions known in the art are not conducive to providing optimal conditions for fertilization. For example, U.S. Pat. No. 4,981,686 is directed towards a non-spermicidal lubricant with healing (i.e., soothing) ingredients and oils, alcohols, detergents, and fragrances that also includes preservatives. U.S. Pat. No. 4,981,686 does not disclose cell viability maintaining agents or fertilization and other function enhancing agents. U.S. Pat. Nos. 6,140,121, 6,593,309, US 2002/0193350, US 2004/0073964 and EP 0 888 117 generally disclose non-spermicidal lubricant comprising polysaccharide agents, such as arabinogalactan (e.g., gum arabic, pectin, or galacturonic acid) and arabinose, galactose and/or hexuronic acid (PCAGH). As described above, the process of fertilization involves binding of sperm to oocyte cells, a multi-step process that subsequently leads to fertilization, and oligo- and polysaccharides interfere with steps in that process. Activated, capacitated sperm, after penetrating through the cumulus oophorus, contacts the zona pellucida (12). Initial sperm:zona pellucida binding is mediated by, among other things, ZP3, a constituent glycoprotein of the zona pellucida, and involves protein-carbohydrate recognition and interaction. For example, the sperm surface receptors associate with O-linked oligosaccharides from protein ZP3 on zona pellucida. Thus, presence of adhesion blocking oligo- and poly-saccharides directly interferes with the physiologic function, thereby negatively impacting the process of fertilization. U.S. Pat. Nos. 6,140,121, 6,593,309, US 2002/ 0193350, US 2004/0073964 and EP 0 888 117 do not disclose non-saccharide containing lubricants. U.S. Pat. Nos. 6,140, 121 , 6,593,309, US 2002/0193350, US 2004/0073964 and EP 0 888 117 also do not disclose cell viability maintaining agents or fertilization and other function enhancing agents. U.S. Pat. Nos. 6,610,331, 6,861,079 and US 2003/0224070 generally disclose a fertility kit comprising a non-spermicidal lubricating jelly containing polysaccharides that influence natural sperm motility. U.S. Pat. Nos. 6,610,331, 6,861,079 and US 2003/0224070 do not disclose non poly-saccharide containing lubricants. U.S. Pat. Nos. 6,610,331, 6,861,079 and US 2003/0224070 also do not disclose cell viability maintaining agents or fertilization and other function enhancing agents. In sum, the disclosures described above are devoid of cell viability maintaining agents, or agents that enhance physiological function, including energy substrates, that we believe to be so essential for maintaining viability of sperm, oocyte and embryo (as well as other cells and tissue), as described above. In fact, not only do these compositions lack the essential cell viability maintaining agents, almost all of the compositions described in the prior art also include EDTA as preservative or buffering agent, which actively and completely removes any residual viability maintaining ions from the solution by chelation. An object of this invention is to provide such compositions. Furthermore, one of the last steps prior to a successful fertilization is the binding and fusing of sperm, that have penetrated the zona pellucida, with the cell membrane of the egg. An object of this invention is to provide compositions that comprise agents that would enhance the binding of sperm cells with oocytes as well as remove certain preservatives, such as EDTA, present in most of the compositions described in the prior art, that prevents this necessary interaction between sperm and egg, negatively impacting the process of fertilization. Another object of this invention is to provide such compositions. Lastly, certain cell surface proteins that are critical for binding between sperm and egg, such as integrins, are naturally present in an inactive conformation on the cells and therefore do not bind their ligands until activated by signals from the environment. An object of this invention is to provide compositions that comprise agents that would enhance the binding of sperm cells with oocytes by activating integrin receptors, among other things. As inclusion of agents in novel compositions that would prime or activate cell surface receptors on sperm and egg for binding to each other would also greatly enhance their fertilization potential. In sum, we have recognized that the compositions described in the prior art lack a number of important agents for maintaining or improving the viability and function of cells, sperm, oocyte, embryos and tissues in vivo and in vitro and that there is a need to develop better compositions, novel articles and methods for use as vaginal and other tissue lubricants and moisturizers. The present invention provides a variety of compositions that are friendly to sperm, oocytes, embryos, cells and tissues and are non-toxic. Additionally, the compositions improve sperm and oocyte function and survival as well as a chance of the successful fertilization. Thus, these described compositions are useful for couples trying to conceive (naturally as well as using a variety of assisted reproduction techniques). The present invention also provides methods of preparation and use of the novel compositions. The present invention further provides other related advantages.

Additionally, certain medical and/or physical conditions deem it advisable or even necessary to use vaginal and surgical lubricants. For example, a lubricant is useful under conditions of postmenopausal vaginal atrophy or post hysterectomy or generally during inadequate mucus production.

Medical instrument insertion into bodily orifices for examination or treatment also necessitates the use of a lubricant, such as for proctologic examination and the like. There is a similar need to develop better compositions, novel articles and methods for use in such applications that do not adversely affect the cell and tissue viability or function. An object of this invention is to provide such product.

For a number of years now the use of artificial insemination and of assisted reproduction techniques (ART) has allowed physicians to treat fertility issues in individuals. These techniques have also benefited from methods for storing cells, sperm, oocytes or embryos for use at different time and/or location. The steps and methods involved, some of which are optional, are: collection of cells, sperm, egg or embryo from humans and other animals; washing the collected samples (for example, washing semen to isolate the sperm-rich fraction, or washing eggs); subsequent processing to obtain viable and functional cells; culturing of cells; the process of in vitro fertilization to develop embryos; storage of cells (in extended culture, refrigerated or cryogenic state) for later use; reprocessing prior to transfer to female; and transfer to female in order to establish pregnancy. A number of compositions for almost each of the steps and methods have been extensively described in the art. For example, preservation of sperm is well known in the art (including U.S. Pat. Nos. 4,267,268, 6,864,046). However, the current compositions are sub-optimal and the compositions that improve viability and/or function of the sample in each of these steps would provide additional benefits during various steps and methods used in artificial insemination and ART. An object of this invention is to provide such product. For example, improved compositions for semen and sperm collection that contain viability maintaining agents or fertilization and other function enhancing agents would greatly improve the chances of sperm-egg binding, thereby improving the fertilization potential, among other things. Similarly, use of novel compositions containing viability maintaining agents or fertilization and other function enhancing agents in sperm wash and sperm isolation media would also improve the chances of sperm-egg binding, thereby improving the fertilization potential, among other things. Similarly, use of novel compositions containing viability maintaining agents or fertilization and other function enhancing agents in in vitro fertilization media would also improve the chances of sperm-egg binding, thereby improving the fertilization potential, among other things. An object of this invention is to provide such product. The present invention further provides compositions that do not harm cells, sperm, oocytes, embryos, tissues or organs and furthermore that improve their viability and function during culture, during storage, transportation and during in vivo and in vitro use. Additionally, compositions are provided for use in various artificial insemination and assisted reproduction techniques in humans and animals. The present invention also provides novel articles, and systems as well as methods of preparation and use of the novel compositions. In addition, the present invention provides other related advantages.

SUMMARY OF THE INVENTION

The compositions, methods of preparation and various applications of novel water-based media, solutions, moisturizers and lubricants are provided. The present invention also provides novel articles, and systems as well as methods of preparation and use of the novel compositions.

The novel water-based compositions comprise of an aqueous solution with optimum pH and osmolality to mimic biological fluids. In a preferred embodiment, such water-based compositions are useful as non-spermicidal vaginal lubricants that are sperm friendly, egg friendly and facilitate fertilization. The water-based solutions may further comprise of sperm and other cell viability maintaining agents, sperm and other cell energy-boosting agents, antioxidants and oxygen scavengers, fertilization facilitation agents, embryo attachment facilitation agents and/or other physiologic function enhancing agents. It is understood that the examples are for illustration only and are not limiting.

Within yet another aspect, methods and compositions are provided for improving human and other animal reproduction using natural or artificial means. The novel compositions can also be used in combination with articles and systems to facilitate fertilization.

The present invention further provides compositions, articles, systems and methods of preparation and use of compositions that do not harm cells, tissues or organs and furthermore that improve their viability and function during culture, during storage, transportation and during in vivo and in vitro use.

Various references incorporated in this patent describe in more detail certain procedures, applications or compositions. Each of these references is incorporated herein by reference in their entirety as if each were individually noted for incorporation.

DETAILED DESCRIPTION OF THE INVENTION

This invention provides compositions, articles, systems, methods of preparation and use for various applications of novel water-based media, solutions, moisturizers and lubricants.

As used herein, the term "viability maintaining agent", unless otherwise specified, refers to agents that are harmless to cell, sperm, oocyte, embryo or tissue and, furthermore, maintain or increase their viability. Examples of viability maintaining agents include, but are not limited to, naturally occurring or synthetic ions and salts, such as calcium, sodium, potassium or magnesium ions and salt. The viability maintaining agent or agents also comprise other ions, salts, lipids, small molecules, carbon monoxide, carbon dioxide, nitric oxide, nucleosides, nucleotides, sugars, peptides, proteins, and chemical, functional and/or physiological equivalents.

As used herein, the term "aqueous lubricant base", unless otherwise specified, refers to water-based compositions containing a lubricious agent in an aqueous balanced salt solution. Examples of lubricious agents include, but are not limited to, glycerol, HISPAGEL, arabinogalactan, PCAGH, dextran, polyacrylic acid, carbomer, polyethylene oxide, Pluronic-127, methylcellulose, hydroxymethyl cellulose, hydroxyethyl cellulose, hydroxypropyl methylcellulose, polyethylene glycol, propylene glycol, hydroxypropyl guar, plant oils, methylparaben, proteins, nucleic acids, petroleum jelly, a combination thereof or other agents that are chemically, functionally, or physiologically equivalent or similar.

As used herein, the term "balanced salt solution", unless otherwise specified, refers to aqueous solutions that have balanced pH and osmolality. Examples of pH buffering agents include, but are not limited to, salts of phosphates, borates, citrates, ascorbates, carbonates, bicarbonates, TRIS, HEPES, or a mixture thereof. Examples of osmotically active agents useful for balancing osmolality of a composition include, but are not limited to, sodium ions, potassium ions, chloride ions, bicarbonate ions, glucose, sucrose, peptides, proteins, a combination thereof or other agents that are chemically, functionally, or physiologically equivalent or similar.

As used herein, the term "enhanced physiological function", unless otherwise specified, refers to improvements in the potential of cell, sperm, oocyte, embryo or tissue to perform their natural function. Examples of enhanced physiological function include, but are not limited to, the increase in the potential of sperm to fertilize, the increase in the potential of oocyte to fertilize, increase in the potential of embryo to develop, and increase the potential of fertilized embryo to attach.

As used herein, the term "sperm activation", unless otherwise specified, refers to the process of converting non-motile, functionally inactive sperm to a sperm in a state that is capable of fertilization. Examples of sperm activation processes include, but are not limited to, decreasing sperm immotility, and inducing or improving sperm capacitation. Examples of sperm activation agent or agents include, but are not limited to, ions (such as bicarbonate, sodium, calcium, magnesium and manganese), salts, hyaluronidase (such as PH-20), albumin, high-density lipoprotein, progesterone, peptides, nucleosides, nucleotides, cyclic AMP, small molecules, proteins, antibodies, chemokine, cytokines, prostaglandins, caffeine, aspirin, carbon monoxide, carbon dioxide, nitric oxide, a combination thereof or other agents that are chemically, functionally, or physiologically equivalent or similar. As another example, the sperm are stored in a functionally inactive state in the cauda epididymis in an environment that contains high concentration of potassium ions, low sodium ions and very low bicarbonate ions (24). However, the composition of capacitation-inducing oviductal fluid and media comprises high concentration of various ions (such as sodium, calcium and bicarbonate) and low concentrations of others (such as potassium (17)).

As used herein, the term "energy-boosting agent", unless otherwise specified, refers to natural or synthetic substances that provide energy substrates to cell, sperm, oocyte, embryo or tissue. Examples of energy-boosting agents include, but are not limited to, adenosine triphosphate (ATP), pyruvate, glucose, lactose, other sugars, lactate, glycerolphosphorylcholine, other lipids, carnitine, amino acids, peptides, proteins, a combination thereof or other agents that are chemically, functionally, or physiologically equivalent or similar.

As used herein, the term "scavenger", unless otherwise specified, refers to natural or synthetic substances that react with and/or prevent damaging free-radicals from causing damage to deoxyribonucleic acid (DNA), ribonucleic acid (RNA), peptide, protein, or the membrane, organelle, structure and function of cell, sperm, oocytes, embryo and tissue. Examples of scavengers include, but are not limited to, vitamin E, Vitamin C, niacin, riboflavin, niacinamide, glutathione, NADH, other anti-oxidants, a combination thereof or other agents that are chemically, functionally, or physiologically equivalent or similar.

As used herein, the term "fertilization facilitator", unless otherwise specified, refers to natural or synthetic substances that remove the agents that may hinder the process of fertilization or that facilitate the process of fertilization. As an example, the fertilization facilitators may function by increasing the potential of sperm and egg surface receptors and ligands to interact. Examples of fertilization facilitators include, but are not limited to, ions (such as magnesium, manganese, bicarbonate and zinc), hyaluronidase (such as PH-20), albumin, high-density lipoprotein, progesterone, panthenol, caffeine, L-carnitine, cyclic-AMP, aspirin, activators of CD9 protein, activators of surface receptors (such as activators integrins), a combination thereof or other agents that are chemically, functionally, or physiologically equivalent or similar.

The term "reproductive tissue", unless otherwise specified, refers to human or other animal tissues involved in the process of reproduction. Examples of reproductive tissue include, without limit, mucous, vaginal, urethral, and penal tissue, and and skin surrounding vaginal and penal tissue among others.

The term "organ", unless otherwise specified, refers to any type of human or other animal organs. Examples of organs include, without limit, reproductive organs (such as vagina, penus), kidney, heart, skin, lung, and liver, among others.

The term "cells", unless otherwise specified, refers to any type of human or other animal cells. Examples of cells include, without limit, sperm, oocyte, and embryo, among others.

The compositions and articles are generally prepared and/or produced by any method, including combining the active ingredients in the appropriate amounts and concentrations. Other active or inactive agents selected by one of skill in the art can optionally be added. The absolute weight of a given agent included in a composition can vary widely. The compositions are preferably sterile and the most preferred method of sterilization is passing through a 0.2 micron filter.

I. Lubricant and Moisturizer Compositions and Applications

This invention is partly a result of our unexpected finding that use of viability maintaining agents and/or fertilization and other physiological function enhancing agents in lubricants and moisturizers greatly improves the viability of biological cells and tissues as well as improves their function. For example, when spermatozoa are incubated in various buffers for 30 minutes and then analyzed for viability using a FACS assay (as described in Example 2), we find (Table I) that there is almost no loss in viability of spermatozoa incubated with lubricants that contain divalent ions as viability maintaining agents (Novel Composition 1 and Novel Composition 2) as compared to the lubricants that don't, (such as K-Y jelly, a lubricant known to be spermicidal (18-22)). An even more surprising result was our finding that the viability of spermatozoa can be dramatically improved over commercially available non-spermicidal lubricants (such as Pre-Seed), by the presence of divalent ions as viability maintaining agents in lubricant compositions. Several other lubricious agents, including glycerol, propylene glycol, and polyethylene glycol, when included as aqueous lubricant base components in the novel lubricant compositions of this invention (that also contain viability maintaining agents) gave results very similar to the ones obtained with the Novel Composition 1 and Novel Composition 2 and shown here.

TABLE I

| Lubricant | Relative percentage of dead spermatozoa |
| --- | --- |
| K-Y Jelly | 100% |
| Pre-Seed | 44% |
| Novel Composition 1 | 1% |
| Novel Composition 2 | 1% |

In a preferred embodiment, novel water-based compositions are provided, comprising viability maintaining agent or agents in aqueous lubricant base. The composition of this invention preferably has an optimum pH, osmolality and viscosity. Within certain embodiments, the compositions of this invention further comprise agent or agents that enhance physiological function. Within certain related aspects, the agent or agents that enhance physiological function comprise sperm activation agent, energy-boosting agent, scavenger(s), fertilization facilitator(s), embryo implantation facilitators or a mixture thereof.

In another aspect, novel water-based compositions are provided, comprising agent or agents that enhance physiological function in an aqueous lubricant base. The compositions of this invention preferably have an optimum pH, osmolality and viscosity. Within certain related aspects, the agent or agents that enhance physiological function comprise sperm activation agent, energy-boosting agent, scavenger(s), fertilization facilitator(s), or a mixture thereof. In a related aspect, the compositions of this invention further comprise viability maintaining agent or agents.

In another aspect, novel water-based compositions are provided that are devoid of certain preservatives and buffers that affect viability or function of cell, sperm, oocyte, embryo or tissues. Examples of the non-desired preservatives include, without limit, EDTA, cyclic-RGD peptide and certain other proteins, glycoproteins, sugars or oligo- and poly-saccharides that inhibit cell-cell and cell-matrix interaction. Within certain related embodiments, the preferred non-desired agent is EDTA. Within certain other related embodiments, the preferred non-desired agents are certain glycoproteins, sugars or oligo- and poly-saccharides that inhibit cell-cell and cell-matrix interaction. The composition of this invention preferably has an optimum pH, osmolality and viscosity. Within certain embodiments, the compositions of this invention further comprise agent or agents that enhance physiological function. In a related aspect, the compositions of this invention further comprise viability maintaining agent or agents. In another related aspect, the compositions of this invention further comprise agent or agents that enhance physiological function. Within certain related aspects, the agent or agents that enhance physiological function comprise sperm activation agent, energy-boosting agent, scavenger(s), fertilization facilitator(s) or a mixture thereof.

Within certain embodiments, aqueous lubricant base may be as described above and preferably comprises glycerol, HISPAGEL, dextran, polyacrylic acid, carbomer, polyethylene oxide, methylcellulose, hydroxyethyl cellulose, hydroxypropyl methylcellulose, polyethylene glycol, propylene glycol, PLURONIC-127, proteins, nucleic acids or petroleum jelly, or a combination thereof in an aqueous salt solution with balanced pH and osmolality. Within certain other embodiments, aqueous lubricant base preferably comprises hydroxypropyl methylcellulose. Within certain other embodiments, aqueous lubricant base preferably comprises propylene glycol, or glycerol or a mixture thereof, as they have far greater water-binding capacities than a number of other humectants, as describe in the U.S. Pat. No. 5,800,807 on various ophthalmic compositions. Within a related aspect, the provided concentration (w/v) of balanced salt solution in aqueous lubricant base is between 1% and 99.999%, preferably between 75% and 99.99%, and most preferably between 95% and 99.9%. Within certain embodiments, optimum pH of the composition is in the range of 5.0 and 9.0, preferably between 7.0 and 8.5 and most preferably between 7.8 and 8.2; optimum osmolality is between 200 and 700 mOsm/kg, preferably between 250 and 500 mOsm/kg, and most preferably between 300 and 400 mOsm/kg; and optimum viscosity, expressed as ratio with the viscosity of a balanced salt solution such as phosphate buffered saline (PBS), is between 1.0 and 5.0, preferably between 1.0 and 3.5, and most preferably between 1.0 and 2.5. Within certain related embodiments, pH buffering agents comprise phosphate salts, borate salts, citrate salts, ascorbate salts, carbonate salts, bicarbonate salts, or a mixture thereof. Within certain further related aspects, other buffering agents, such as TRIS, PIPES, HEPES and the like may be added to these solutions. Sodium hydroxide is preferably added to adjust the pH. Within certain further related embodiments, osmolytes comprise sodium ions, potassium ions, inositol, betaine, sorbitol, peptides or glutamine. Within certain further related embodiments, the concentration of the osmolyte potassium ions is low, between 0.001 micromolar (uM) and 12.5 millimolar (mM), preferably between 0.1 uM and 10 mM, and most preferably between 10 uM and 5 mM.

Within certain embodiments, the preferred viability maintaining agent is ionic, and the preferable ions are calcium or magnesium. Within a related aspect, the composition comprises one or more viability maintaining agents. Within another related aspect, the provided concentration of viability maintaining agent is between 0.001 micromolar (uM) and 1 molar (M), preferably between 0.01 millimolar (mM) and 10 mM, and most preferably between 0.1 mM and 5 mM. Within certain other embodiments, the preferred viability maintaining agent is selected from carbon monoxide, carbon dioxide, nitric oxide or a mixture thereof.

Within certain embodiments, the preferred sperm activation agent is ionic, and the preferable ions are calcium, magnesium, manganese, or bicarbonate. Within a related aspect, the composition comprises one or more sperm activation agents. Within another related aspect, the provided concentration of sperm activation agent is between 0.001 micromolar (uM) and 1 molar (M), preferably between 0.01 uM and 50 mM, and most preferably between 1 uM and 30 mM. Within another further related aspect, the most preferred sperm activation agent is calcium ion and the provided concentration of calcium is preferably between 10 uM and 10 mM, and most preferably between 500 uM and 5 mM. Within certain other further related aspect, the most preferred sperm activation agent is magnesium ion and the provided concentration of calcium is preferably between 10 uM and 10 mM, and most preferably between 500 uM and 5 mM. Within certain other further related aspect, the most preferred sperm activation agent is bicarbonate ion and the provided concentration of bicarbonate ion is preferably between 100 uM and 50 mM, and most preferably between 10 mM and 30 mM. Within certain other embodiments, the preferred sperm activation agent is cyclic AMP, caffeine, aspirin, carbon monoxide or a mixture thereof. Within certain related embodiments, the preferred sperm activation agent is caffeine. Within certain other related embodiments, the preferred sperm activation agent is selected from hyaluronidase (such as PH-20), albumin, high-density lipoprotein, progesterone or a mixture thereof.

Within certain embodiments, the preferred energy-boosting agent is pyruvate, lactate or a mixture thereof. Within certain related embodiments, the concentration of energy-boosting agent is between 0.0001 uM and 100 mM, preferably between 0.01 uM and 10 mM, and most preferably between 1 uM and 1 mM.

Within certain embodiments, the preferred scavenger is vitamin E, Vitamin C, niacin, riboflavin, niacinamide or a mixture thereof. Within certain related embodiments, the concentration of scavenger is between 0.0001 uM and 100 mM, preferably between 0.01 uM and 10 mM, and most preferably between 1 uM and 1 mM.

Within certain embodiments, the preferred fertilization facilitator is chosen from magnesium ions, manganese ions, bicarbonate ions, hyaluronidase, progesterone, panthenol, caffeine, L-carnitine, cyclic-AMP or a mixture thereof. Within certain related embodiments, the concentration of fertilization facilitator is between 0.0001 uM and 100 mM, preferably between 0.01 uM and 10 mM, and most preferably between 1 uM and 2 mM.

Within another aspect, the compositions of this invention are devoid of preservatives that affect viability or function of cell, sperm, oocyte, embryo or tissues. Examples of the non-desired agents include, without limit, EDTA, cyclic-RGD peptide and certain glycoproteins, sugars or oligo-saccharides that inhibit cell-cell and cell-matrix interaction. Within certain related embodiments, the preferred non-desired preservative is EDTA. Within certain other related embodiments, the preferred non-desired preservatives are certain glycoproteins, sugars or oligo-saccharides that inhibit cell-cell and cell-matrix interaction.

Within yet another aspect, the compositions of this invention contain the preservatives that do not affect viability or function of cell, sperm, oocyte, embryo or tissues. Examples of the preferred desirable preservatives that do not affect viability or function of cell, sperm, oocyte, embryo or tissues include, without limit, boric acid, ascorbic acid, sodium borate, methyl paraben or a combination thereof. Within certain related embodiments, the concentration of desirable preservative is between 0.00001% and 10%, preferably between 0.0001% and 5%, and most preferably between 0.001% and 1%.

Within certain other embodiments, the compositions of this invention contain other pharmaceutically useful agents including, without limit, anti-itch agents, anesthetic agents, estrogenic agents, antibiotic agents, antiviral agents, anti-fungal agents, steroids, therapeutic drugs, drug delivery vehicles and others, and including combinations thereof. Penicillin, streptomycin, gentamycin, or mixtures thereof are preferred antibiotics.

Within certain other embodiments, the compositions of this invention contain other embryo implantation potential enhancing agents including, without limit, hyaluronan.

Within certain other aspects, the composition of this invention is preferably non-staining, non-irritating, clear, odorless, without undesired preservatives and non-spermicidal.

Within certain embodiments, the composition of this invention may be in the form of a solution, gel, foam, cream, jelly, suppository, douche, film, dissolvable film or the like. Additionally, the compositions may also be packaged in sterile pre-filled, single use applicators, tubes and other containers. Within certain aspects, a packaging applicator can be designed to allow a minimal contact with skin, thus allowing further reduction of the contamination with harmful micro-organisms such as yeast, bacteria and viruses. Within certain other aspects, the composition may be packaged in a kit containing a tube of composition as a lubricant and an applicator for application to the vagina. Within certain related aspects, the kit may contain multiple such tubes. Within certain further related aspects, the kit may contain other items, such as, without limit, instruction sheets, vitamin pills, fertility monitors, nutracueticals and the like.

Within certain embodiments, the novel water-based compositions may be used as tissue moisturizers and lubricants in human and other animals. Within certain preferred embodiments, the novel water-based compositions are useful as vaginal lubricants and moisturizers. Within certain preferred related aspects, the vaginal lubricants provided are non-spermicidal, sperm-friendly, oocyte-friendly and embryo-friendly. Within certain other preferred aspects, the lubricant compositions provided increase fertilization-potential of sperm and of oocyte. Within certain other preferred aspects, the lubricant compositions provided increase implantation potential of fertilized embryo.

Within certain aspects, the novel lubricants and moisturizers may be used during coitus, in various assistive reproduction techniques, such as ART, and in various other medical and diagnostic procedures in human and other animals.

Within certain aspects, a preferred method of use may be by administration or placement in a vagina prior to or during coitus. The composition may also be used by administration or placement in a vagina prior to or during artificial insemination. Furthermore, the composition may also be used by administration or placement in a vagina prior to or during an in vitro fertilization procedure. In another aspect, the composition may be used by application or administration to a penis prior to or during coitus. The composition may also be used by application or administration to a penis prior to or during an in vitro fertilization or artificial insemination procedure. Examples include, without limit, application or administration of the composition during semen or sperm collection to a penis prior to ejaculation of semen or sperm into a collection vessel, or collection of semen or sperm into a collection vessel containing the composition. Within a related aspect, the composition may be added to the semen or sperm collection vessel prior to, during or subsequent to the collection procedure.

Within certain embodiments, the novel compositions may be used to coat, lubricate and moisturize tissues. Within another aspect, the novel compositions may be used to coat, lubricate and moisturize, surfaces and/or articles. Within a related aspect, the preferred articles are condoms. Within yet another aspect, the composition is used to lubricate the inside, outside or both of a condom. Within yet another aspect, the composition may be used as a lubricant for medical device or hand prior to or during medical or reproductive procedures.

Within yet another aspect, the provided methods and compositions are used in preparing dermatological creams, gels, moisturizers and lubricants to relieve dryness and irritation.

Within yet another aspect, novel water-based compositions are provided for use as a lubricant for delivery of a child at birth.

Within certain embodiments, the novel water-based lubricant compositions may be useful as compositions for collection of various biological samples, such as, without limit, cerebrospinal fluid, biopsy cells, biopsy tissue, cysts, tumors, saliva, stool, buccal swab, tissue, cells, blood, fluid or a mixture thereof. Within certain related aspects, the compositions of this invention preserve viability of the collected biological material. Within certain other aspects, the compositions of this invention are useful as culturing or extending media immediately after collection of biological samples. Within certain other aspects, the compositions of this invention are useful as culturing or extending media immediately for biological samples following their storage in a controlled temperature, heated, refrigerated, frozen or vitrified state.

Within certain embodiments, the novel water-based lubricant compositions may be useful as compositions for collection of various microbiological flora (such as, without limit, bacteria, fungi, virus etc) from biological samples, such as, without limit, cerebrospinal fluid, biopsy cells, biopsy tissue, cysts, tumors, saliva, stool, buccal swab, cells, tissue, fluid, blood or a mixture thereof. Within certain related aspects, the compositions of this invention preserve viability of the collected micro flora. Within certain other aspects, the compositions of this invention are useful as culturing or extending media of the micro flora immediately after collection of biological samples. Within certain other aspects, the compositions of this invention are useful as culturing or extending media of the micro flora immediately for biological samples following their storage in a refrigerated, frozen or vitrified state. Within certain aspects, the micro flora collected using the novel compositions are used in, without limit, development of assays, small molecules, therapeutics, high-throughput screenings etc.

Within certain embodiments, the novel water-based lubricant compositions may be useful as compositions for collection of various biological organs, such as, without limit, vagina, penus, kidney, lung, heart, liver, bone, skin and the like or a mixture thereof. Within certain related aspects, the compositions of this invention preserve viability of the collected organs. Within certain other related aspects, the compositions of this invention physiological function of the collected organs. For example, the compositions of this invention may enhance the function of an organ post-transplantation, by reducing the rejection rate. Within certain other aspects, the compositions of this invention are useful as culturing or extending media immediately after collection of organs. Within certain other aspects, the compositions of this invention are useful as culturing or extending media immediately for organs following their storage in a controlled temperature, room temperature, heated, body temperature, refrigerated, frozen or vitrified state. Within certain other aspects, the compositions of this invention are useful as transportation solutions for organs. Within certain other aspects, the compositions of this invention are useful as transportation solutions for organs. Within certain other aspects, the compositions of this invention improve the viability and/or physiological function of organs during culture, during storage, transportation and during in vivo and in vitro use.

Within certain embodiments, the novel water-based lubricant compositions may be useful as compositions for use during medical treatments for, such as, without limit, wounds, rashes, burns, bruises, transplants and the like.

Within certain aspects, the compositions and articles of this invention are generally prepared and/or produced by any method, including combining the active ingredients in the appropriate amounts and concentrations in a container and mixing. If need be, the mixtures are heated or cooled to aid in solvation of the ingredients. The compositions are preferably sterile and the most preferred method of sterilization is passing through a 0.2 micron filter. Within certain aspects, the compositions of this invention also have a high degree of clarity, preferably a turbidity of less than about 2, as measured with standard turbidimetric procedures known in the art.

II. Media Compositions and Application

The invention further provides novel compositions and for use as media as well as provides methods of use.

Within certain embodiments, the novel water-based compositions may be used as culture and/or extension media for sperm, oocyte, embryo, cells or tissues during their in vitro culture or extension, comprising viability maintaining agent or agents in a balanced salt solution base. The composition of this invention preferably has an optimum pH, osmolality and viscosity. Within certain embodiments, the compositions of this invention further comprise agent or agents that enhance physiological function. Within certain related aspects, the agent or agents that enhance physiological function comprise sperm activation agent, energy-boosting agent, scavenger(s), fertilization facilitator(s) or a mixture thereof. Within certain embodiments, novel water-based compositions provided are devoid of certain preservatives and buffers that affect viability or function of cell, sperm, oocyte, embryo or tissues. Examples of the non-desired preservatives include, without limit, EDTA, cyclic-RGD peptide and certain glycoproteins, sugars or oligo-saccharides that inhibit cell-cell and cell-matrix interaction.

Within certain other aspects, the novel water-based compositions may be used as culture and extension media for sperm, oocyte, embryo, cells or tissues during their in vitro culture or extension, comprising agent or agents that enhance physiological function in a balanced salt solution base. The compositions of this invention preferably have an optimum pH, osmolality and viscosity. Within certain related aspects, the agent or agents that enhance physiological function comprise sperm activation agent, energy-boosting agent, scavenger(s), fertilization facilitator(s), or a mixture thereof. In a related aspect, the compositions of this invention further comprise viability maintaining agent or agents. Within certain embodiments, novel water-based compositions provided are devoid of certain preservatives and buffers that affect viability or function of cell, sperm, oocyte, embryo or tissues. Examples of the non-desired preservatives include, without limit, EDTA, cyclic-RGD peptide and certain glycoproteins, sugars or oligo-saccharides that inhibit cell-cell and cell-matrix interaction.

Within certain embodiments, balanced salt solution base may include, but is not limited to, Iscove's Modified Dulbecco's Medium (IMDM), Dulbecco's Medium Eagle's Medium (DMEM), Roswell Park Memorial Institute (RPMI) media (such as RPMI 1640), Tyrode's buffered salts, Oocyte collection media, TALP, HTF, CZB, T6, Ham's F12, Earle's buffered salts, BWW, Earle's MTF, KSOM, SOF, PBS and the like. Composition of each of these balanced salt solutions is well known in the art and many are commercially available (for example, from ATCC, Fisher Scientific, Invitrogen, VitroLife etc.). Furthermore, other buffering agents, such as TRIS, PIPES, HEPES and the like may be added to these solutions. Additionally, certain other agents, such as serum, albumin, gelatin, vitamins, minerals, amino acids, nucleotides, sucrose, trehalose, ethanol, DMSO, hydroxypropyl methylcellulose and the like, may also be added to the buffered salt solutions. Within related aspects, the provided concentration (w/v) of the balanced salt solution base in the composition is between 50% and 99.999%, preferably between 75% and 99.99%, and most preferably between 95% and 99.9%. Within certain embodiments, optimum pH of the composition is in the range of 5.0 and 9.0, preferably between 7.0 and 8.5 and most preferably between 7.8 and 8.2; optimum osmolality is between 200 and 700 mOsm/kg, preferably between 250 and 500 mOsm/kg, and most preferably between 300 and 350 mOsm/kg; and optimum viscosity, expressed as ratio with the viscosity of a balanced salt solution such as phosphate buffered saline (PBS), is between 1.0 and 5.0, preferably between 1.0 and 2.5, and most preferably between 1.0 and 1.2. Within certain related embodiments, pH buffering agents comprise phosphate salts, borate salts, citrate salts, ascorbate salts, carbonate salts, bicarbonate salts, or a mixture thereof. Sodium hydroxide is preferably added to adjust the pH. Within certain further related embodiments, osmolytes comprise sodium ions, potassium ions, inositol, betaine, sorbitol, peptides or glutamine. Within certain further related embodiments, the concentration of the osmolyte potassium ions is low, between 0.001 micromolar (uM) and 12.5 millimolar (mM), preferably between 0.1 uM and 10 mM, and most preferably between 10 uM and 5 mM.

Within certain embodiments, the preferred viability maintaining agent is ionic, and the preferable ions are calcium or magnesium. Within a related aspect, the composition comprises one or more viability maintaining agents. Within another related aspect, the provided concentration of viability maintaining agent is between 0.001 micromolar (uM) and 1 molar (M), preferably between 0.01 millimolar (mM) and 10 mM, and most preferably between 0.1 mM and 5 mM. Within certain other embodiments, the preferred viability maintaining agent is selected from carbon monoxide, carbon dioxide, nitric oxide or a mixture thereof.

Within certain embodiments, the preferred sperm activation agent is ionic, and the preferable ions are calcium, magnesium, manganese, or bicarbonate. Within a related aspect, the composition comprises one or more sperm activation agents. Within another related aspect, the provided concentration of sperm activation agent is between 0.001 micromolar (uM) and 1 molar (M), preferably between 0.01 uM and 50 mM, and most preferably between 1 uM and 30 mM. Within another further related aspect, the most preferred sperm activation agent is calcium ion and the provided concentration of calcium is preferably between 10 uM and 10 mM, and most preferably between 500 uM and 5 mM. Within certain other further related aspect, the most preferred sperm activation agent is magnesium ion and the provided concentration of calcium is preferably between 10 uM and 10 mM, and most preferably between 500 uM and 5 mM. Within certain other further related aspect, the most preferred sperm activation agent is bicarbonate ion and the provided concentration of bicarbonate ion is preferably between 100 uM and 50 mM, and most preferably between 10 mM and 30 mM. Within certain other embodiments, the preferred sperm activation agent is cyclic AMP, caffeine, aspirin, carbon monoxide or a mixture thereof. Within certain related embodiments, the preferred sperm activation agent is caffeine. Within certain other related embodiments, the preferred sperm activation agent is selected from hyaluronidase (such as PH-20), albumin, high-density lipoprotein, progesterone or a mixture thereof.

Within certain embodiments, the preferred energy-boosting agent is ATP, fructose, glucose, pyruvate, lactose, lactate or a mixture thereof. Within certain related embodiments, the concentration of energy-boosting agent is between 0.0001 uM and 1 M, preferably between 0.01 uM and 100 mM, and most preferably between 1 uM and 25 mM.

Within certain embodiments, the preferred scavenger is vitamin E, Vitamin C, niacin, riboflavin, niacinamide or a mixture thereof. Within certain related embodiments, the concentration of scavenger is between 0.0001 uM and 100 mM, preferably between 0.01 uM and 10 mM, and most preferably between 1 uM and 1 mM.

Within certain embodiments, the preferred fertilization facilitator is selected from magnesium ions, manganese ions, bicarbonate ions, hyaluronidase, progesterone, panthenol, caffeine, L-carnitine, cyclic-AMP or a mixture thereof. Within certain related embodiments, the concentration of fertilization facilitator is between 0.0001 uM and 100 mM, preferably between 0.01 uM and 10 mM, and most preferably between 1 uM and 2 mM.

Within another aspect, the compositions of this invention may be devoid of the preservatives that affect viability or function of cell, sperm, oocyte, embryo or tissues. Examples of the non-desired preservatives include, without limit, EDTA and certain glycoproteins, sugars or oligo-saccharides that inhibit cell-cell and cell-matrix interaction. Within certain related embodiments, the preferred non-desired preservative is EDTA. Within certain other related embodiments, the preferred non-desired preservatives are certain glycoproteins, sugars or oligo-saccharides that inhibit cell-cell and cell-matrix interaction.

Within yet another aspect, the compositions of this invention may contain the preservatives that do not affect viability or function of cell, sperm, oocyte, embryo or tissues. Examples of the preferred desirable preservatives that do not affect viability or function of cell, sperm, oocyte, embryo or tissues include, without limit, boric acid, ascorbic acid, sodium borate, methyl paraben or a combination thereof.

Within certain related embodiments, the concentration of desirable preservative is between 0.00001% and 10%, preferably between 0.0001% and 5%, and most preferably between 0.001% and 1%.

Within certain other embodiments, the compositions of this invention may contain other pharmaceutically useful agents including, without limit, anti-itch agents, anesthetic agents, estrogenic agents, antibiotic agents, steroids, therapeutic drugs, drug delivery vehicles and others, and including combinations thereof. Penicillin, streptomycin, gentamycin, or mixtures thereof are preferred antibiotics.

Within certain embodiments, the compositions of this invention may contain other implantation potential enhancing agents including, without limit, hyaluronan.

Within certain other aspects, the composition of this invention may be in the form of a solution, powder, gel, foam, cream, jelly, or the like. Additionally, the compositions may also be packaged in sterile pre-filled bottles, applicators, tubes and other containers. Within certain aspects, the composition is provided at a higher concentration such that dilution with one or more diluents, such as water, is performed prior to its use in an application. Within certain other aspects, the composition may be packaged in a kit. Within certain related aspects, the kit may contain multiple such tubes. Within certain further related aspects, the kit may contain other items, such as, without limit, instruction sheets and the like.

Within certain preferred aspects, the media compositions provided are non-spermicidal, sperm-friendly, oocyte-friendly and embryo-friendly. Within certain other preferred aspects, the media compositions provided increase fertilization-potential of sperm and of oocyte. Within certain other preferred aspects, the media compositions provided increase implantation potential of fertilized embryo.

Within certain other embodiments, the novel water-based compositions may be useful as media for various steps and methods during artificial insemination or assisted reproduction techniques (ART) or to otherwise treat fertility issues in humans and other animals in vitro. Examples of such procedures include, without limit, sperm collection, sperm washing, sperm extension, oocyte collection, oocyte washing, in vitro fertilization and the like. For example, the novel water-based compositions may be used as medium for washing sperm, oocyte, embryo, cells or tissues. Within another aspect, the compositions may be useful for or during the isolation of motile sperm from a sample. Within yet another aspect, the provided methods and compositions are useful in improving sperm-egg interactions, thereby increasing the chance of fertilization, in vivo and in vitro. Within another aspect, methods and compositions are provided for improving the process of in vitro fertilization, artificial insemination or other fertility related treatments.

Within certain embodiments, the novel water-based compositions may be useful as wash media in various steps and methods during artificial insemination or assisted reproduction techniques (ART) or to otherwise treat fertility issues in humans and other animals in vitro. Examples of such procedures include, without limit, sperm collection, sperm washing, sperm extension, oocyte collection, oocyte washing, in vitro fertilization and the like. For example, the novel water-based compositions may be used as medium for washing sperm, oocyte, embryo, cells or tissues. Within another aspect, the compositions may be useful for or during the isolation of motile sperm from a sample. Within yet another aspect, the provided methods and compositions are useful in improving sperm-egg interactions, thereby increasing the chance of fertilization, in vivo and in vitro. Within another aspect, methods and compositions are provided for improving the process of in vitro fertilization, artificial insemination or other fertility related treatments.

Within certain other aspects, the novel water-based compositions may be used in vitro as culturing medium or extending medium for development of specialized cells, such as embryos and stem cells, using improvements in cell-cell binding, such as sperm-egg binding.

Within yet another aspect, methods and compositions are provided for development of specialized cells, such as embryos and stem cells, using improvements in cell-cell binding, such as sperm-egg binding.

Within other aspects, methods for increasing survival of sperm, oocyte, embryo, cells, tissue are provided that include contacting them with a composition of this invention. In yet other aspects, methods for preserving the function of sperm, eggs and cells, for reducing the loss of sperm-function (and egg, oocyte and cell-function) and sperm, egg, oocyte & cell damage are provided. In yet other aspects, methods for improving the function of sperm and cells are provided. Within related aspects, medium for storing sperm, oocyte, embryo or cells is provided.

Within certain embodiments, the novel water-based media compositions may be useful as compositions for collection of various biological samples, such as, without limit, cerebrospinal fluid, biopsy cells, biopsy tissue, cysts, tumors, saliva, stool, buccal swab, tissue, cells, fluid, blood, or a mixture thereof. Within certain related aspects, the compositions of this invention preserve viability of the collected biological material. Within certain other aspects, the compositions of this invention are useful as culturing or extending media immediately after collection of biological samples. Within certain other aspects, the compositions of this invention are useful as culturing or extending media immediately for biological samples following their storage in a controlled temperature, heated, refrigerated, frozen or vitrified state.

Within certain embodiments, the novel water-based media compositions may be useful as compositions for collection of various microbiological flora (such as, without limit, bacteria, fungi, virus etc) from biological samples, such as, without limit, cerebrospinal fluid, biopsy cells, biopsy tissue, cysts, tumors, saliva, stool, buccal swab, cells, tissue, fluid, blood or a mixture thereof. Within certain related aspects, the compositions of this invention preserve viability of the collected micro flora. Within certain other aspects, the compositions of this invention are useful as culturing or extending media of the micro flora immediately after collection of biological samples. Within certain other aspects, the compositions of this invention are useful as culturing or extending media of the micro flora immediately for biological samples following their storage in a controlled temperature, heated, refrigerated, frozen or vitrified state. Within certain aspects, the micro flora collected using the novel compositions are used in, without limit, development of assays, small molecules, therapeutics, high-throughput screenings etc.

Within certain aspects, the compositions and articles of this invention are generally prepared and/or produced by any method, including combining the active ingredients in the appropriate amounts and concentrations in a container and mixing. If need be, the mixtures are heated or cooled to aid in solvation of the ingredients. The compositions are preferably sterile and the most preferred method of sterilization is passing through a 0.2 micron filter. Within certain aspects, the compositions of this invention also have a high degree of clarity, preferably a turbidity of less than about 2, as measured with standard turbidimetric procedures known in the art.

Within certain embodiments, the novel water-based lubricant compositions may be useful as compositions for collection of various biological organs, such as, without limit, vagina, penus, kidney, lung, heart, liver, bone, skin and the like or a mixture thereof. Within certain related aspects, the compositions of this invention preserve viability of the collected organs. Within certain other related aspects, the compositions of this invention physiological function of the collected organs. For example, the compositions of this invention may enhance the function of an organ post-transplantation, by reducing the rejection rate. Within certain other aspects, the compositions of this invention are useful as culturing or extending media immediately after collection of organs. Within certain other aspects, the compositions of this invention are useful as culturing or extending media immediately for organs following their storage in a controlled temperature, room temperature, heated, body temperature, refrigerated, frozen or vitrified state. Within certain other aspects, the compositions of this invention are useful as transportation solutions for organs. Within certain other aspects, the compositions of this invention are useful as transportation solutions for organs. Within certain other aspects, the compositions of this invention improve the viability and/or physiological function of organs during culture, during storage, transportation and during in vivo and in vitro use.

Within certain embodiments, the novel water-based lubricant compositions may be useful as compositions for use during medical treatments for, such as, without limit, wounds, rashes, burns, bruises, transplants and the like.

Within certain embodiments, the sample is obtained from animals, including human, bovine, canine, equine, porcine, ovine, avian, rodent or rare and exotic species or is artificially generated.

III. Storage Media Compositions and Applications

Within certain embodiments, the novel water-based compositions may be used as storage media for preserving sperm, oocyte, embryo, cells or tissues during their storage in a controlled temperature, heated, refrigerated, frozen or vitrified state, comprising viability maintaining agent or agents in a storage solution base. The composition of this invention preferably has an optimum pH, osmolality and viscosity. Within certain embodiments, the compositions of this invention further comprise agent or agents that enhance physiological function. Within certain related aspects, the agent or agents that enhance physiological function comprise sperm activation agent, energy-boosting agent, scavenger(s), fertilization facilitator(s) or a mixture thereof. Within certain embodiments, novel water-based compositions provided are devoid of certain preservatives and buffers that affect viability or function of cell, sperm, oocyte, embryo or tissues. Examples of the non-desired preservatives include, without limit, EDTA, cyclic-RGD peptide and certain glycoproteins, sugars or oligo-saccharides that inhibit cell-cell and cell-matrix interaction.

Within certain other aspects, the novel water-based compositions may be used as storage media for preserving sperm, oocyte, embryo, cells or tissues during their storage in a controlled temperature, heated, refrigerated, frozen or vitrified state, comprising agent or agents that enhance physiological function in a storage solution base. The compositions of this invention preferably have an optimum pH, osmolality and viscosity. Within certain related aspects, the agent or agents that enhance physiological function comprise sperm activation agent, energy-boosting agent, scavenger(s), fertilization facilitator(s), or a mixture thereof. In a related aspect, the compositions of this invention further comprise viability maintaining agent or agents. Within certain embodiments, novel water-based compositions provided are devoid of certain preservatives and buffers that affect viability or function of cell, sperm, oocyte, embryo or tissues. Examples of the non-desired preservatives include, without limit, EDTA, cyclic-RGD peptide and certain glycoproteins, sugars or oligo-saccharides that inhibit cell-cell and cell-matrix interaction.

Within certain embodiments, storage solution base may comprise balanced salt solution that includes, but is not limited to, IMDM, DMEM, RPMI media, Tyrode's buffered salts, TALP, HTF, CZB, T6, Ham's F12, Earle's buffered salts, BWW, Earle's MTF, KSOM, SOF, and the like. Composition of each of these balanced salt solutions is well known in the art and many are commercially available (for example, from ATCC, Fisher Scientific, Invitrogen, VitroLife etc.). Furthermore, buffering agents, such as TRIS, PIPES, HEPES and the like may be added to these solutions. Additionally, certain other agents, such as Trehalose, DMSO, ethanol, other alcohols, glycerol, ethylene glycol, propylene glycol, hydroxypropyl methylcellulose, serum, albumin, gelatin, vitamins, minerals, amino acids, nucleotides, sucrose, other sugars and the like, may also be added to the balanced salt solutions. Within related aspects, the provided concentration (w/v) of balanced salt solution in the storage solution base is between 50% and 99.999%, preferably between 75% and 99%, and most preferably between 80% and 93%. Within certain embodiments, optimum pH of the composition is in the range of 5.0 and 9.0, preferably between 7.0 and 8.5 and most preferably between 7.8 and 8.2; optimum osmolality is between 200 and 700 mOsm/kg, preferably between 250 and 500 mOsm/kg, and most preferably between 300 and 350 mOsm/kg; and optimum viscosity, expressed as ratio with the viscosity of a balanced salt solution such as phosphate buffered saline (PBS), is between 1.0 and 5.0, preferably between 1.0 and 4.0, and most preferably between 1.0 and 3.0. Within certain related embodiments, pH buffering agents comprise phosphate salts, borate salts, citrate salts, ascorbate salts, carbonate salts, bicarbonate salts, or a mixture thereof. Sodium hydroxide is preferably added to adjust the pH. Within certain further related embodiments, osmolytes comprise sodium ions, potassium ions, inositol, betaine, sorbitol, peptides or glutamine. Within certain further related embodiments, the concentration of the osmolyte potassium ions is low, between 0.001 micromolar (uM) and 12.5 millimolar (mM), preferably between 0.1 uM and 10 mM, and most preferably between 10 uM and 5 mM.

Within certain embodiments, the preferred viability maintaining agent is ionic, and the preferable ions are calcium or magnesium. Within a related aspect, the composition comprises one or more viability maintaining agents. Within another related aspect, the provided concentration of viability maintaining agent is between 0.001 micromolar (uM) and 1 molar (M), preferably between 0.01 millimolar (mM) and 10 mM, and most preferably between 0.1 mM and 5 mM. Within certain other embodiments, the preferred viability maintaining agent is selected from carbon monoxide, carbon dioxide, nitric oxide or a mixture thereof.

Within certain embodiments, the preferred sperm activation agent is ionic, and the preferable ions are calcium, magnesium, manganese, or bicarbonate. Within a related aspect, the composition comprises one or more sperm activation agents. Within another related aspect, the provided concentration of sperm activation agent is between 0.001 micromolar (uM) and 1 molar (M), preferably between 0.01 uM and 50 mM, and most preferably between 1 uM and 30 mM. Within another further related aspect, the most preferred sperm activation agent is calcium ion and the provided concentration of calcium is preferably between 10 uM and 10 mM, and most preferably between 500 uM and 5 mM. Within certain other further related aspect, the most preferred sperm activation agent is magnesium ion and the provided concentration of calcium is preferably between 10 uM and 10 mM, and most preferably between 500 uM and 5 mM. Within certain other further related aspect, the most preferred sperm activation agent is bicarbonate ion and the provided concentration of bicarbonate ion is preferably between 100 uM and 50 mM, and most preferably between 10 mM and 30 mM. Within certain other embodiments, the preferred sperm activation agent is cyclic AMP, caffeine, aspirin, carbon monoxide or a mixture thereof. Within certain related embodiments, the preferred sperm activation agent is caffeine. Within certain other related embodiments, the preferred sperm activation agent is selected from hyaluronidase (such as PH-20), albumin, high-density lipoprotein, progesterone or a mixture thereof.

Within certain embodiments, the preferred energy-boosting agent is ATP, fructose, glucose, pyruvate, lactose, lactate or a mixture thereof. Within certain related embodiments, the concentration of energy-boosting agent is between 0.0001 uM and 1 M, preferably between 0.01 uM and 100 mM, and most preferably between 1 uM and 25 mM.

Within certain embodiments, the preferred scavenger is vitamin E, Vitamin C, niacin, riboflavin, niacinamide or a mixture thereof. Within certain related embodiments, the concentration of scavenger is between 0.0001 uM and 100 mM, preferably between 0.01 uM and 10 mM, and most preferably between 1 uM and 1 mM.

Within certain embodiments, the preferred fertilization facilitator is magnesium ions, manganese ions, bicarbonate ions, hyaluronidase, progesterone, panthenol, caffeine, L-carnitine, cyclic-AMP or a mixture thereof. Within certain related embodiments, the concentration of fertilization facilitator is between 0.0001 uM and 100 mM, preferably between 0.01 uM and 10 mM, and most preferably between 1 uM and 2 mM.

Within another aspect, the compositions of this invention may be devoid of the preservatives that affect viability or function of cell, sperm, oocyte, embryo or tissues. Examples of the non-desired preservatives include, without limit, EDTA and certain glycoproteins, sugars or oligo- and poly-saccharides that inhibit cell-cell and cell-matrix interaction. Within certain related embodiments, the preferred non-desired preservative is EDTA. Within certain other related embodiments, the preferred non-desired preservatives are certain glycoproteins, sugars or oligo- and poly-saccharides that inhibit cell-cell and cell-matrix interaction.

Within yet another aspect, the compositions of this invention may contain the preservatives that do not affect viability or function of cell, sperm, oocyte, embryo or tissues. Examples of the preferred desirable preservatives that do not affect viability or function of cell, sperm, oocyte, embryo or tissues include, without limit, boric acid, ascorbic acid, sodium borate, methyl paraben or a combination thereof. Within certain related embodiments, the concentration of desirable preservative is between 0.00001% and 10%, preferably between 0.0001% and 5%, and most preferably between 0.001% and 1%.

Within yet another aspect, the compositions of this invention may contain "protective agents" that reduce the loss of viable cells, tissues or organs during their storage in a controlled temperature, heated, refrigerated, frozen or vitrified state. Examples of the preferred protective agents include, without limit, hydroxypropyl methylcellulose, DMSO, albumin, serum, glycerol, trehalose, PCAGH, poly-saccharides, carbon monoxide, carbon dioxide, glycoproteins or a combination thereof. Within certain related embodiments, the concentration of desirable preservative is between 0.01% and 50%, preferably between 0.1% and 25%, and most preferably between 1% and 10%.

Within certain other embodiments, the compositions of this invention may contain other pharmaceutically useful substances including, without limit, anti-itch agents, anesthetic agents, estrogenic agents, antibiotic agents, steroids, therapeutic drugs, drug delivery vehicles and others, and including combinations thereof. Penicillin, streptomycin, gentamycin, or mixtures thereof are preferred antibiotics.

Within certain embodiments, the compositions of this invention may contain other implantation potential enhancing agents including, without limit, hyaluronan.

Within certain other aspects, the composition of this invention may be in the form of a solution, gel, foam, cream, jelly, or the like. Additionally, the compositions may also be packaged in sterile pre-filled, applicators, tubes and other containers. Within certain aspects, the composition is provided at a higher concentration such that dilution with one or more diluents, such as water, is performed prior to its use in an application. Within certain other aspects, the composition may be packaged in a kit. Within certain related aspects, the kit may contain multiple such tubes. Within certain further related aspects, the kit may contain other items, such as, without limit, instruction sheets and the like.

Within certain preferred aspects, the media compositions provided are non-spermicidal, sperm-friendly and increase fertilization-potential. Within certain other preferred aspects, the media compositions provided increase the implantation potential of the embryo.

Within certain embodiments, the novel water-based compositions may be used as storage media during artificial insemination or assisted reproduction techniques (ART) or to otherwise treat fertility issues in humans and other animals. Examples include, without limit, sperm storage, oocyte storage, cell storage, embryo storage, tissue storage and the like.

Within certain aspects, the novel water-based compositions and methods may be useful in reducing the loss of viable sperm, oocyte, embryo, cells or tissues during their storage in a controlled temperature, heated, refrigerated, frozen or vitrified state.

Within yet other aspects, the novel water-based compositions and methods may be useful in reducing the loss of functional sperm, oocyte, embryo, cells or tissues during their storage in a controlled temperature, heated, refrigerated, frozen or vitrified state.

Within certain aspects, the novel water-based compositions and methods may be useful for increasing the viability of sperm, oocyte, embryo, cells or tissues during their storage in a controlled temperature, heated, refrigerated, frozen or vitrified state.

Within yet other aspects, the novel water-based compositions and methods may be useful increasing the number of functional sperm, oocyte, embryo, cells or tissues during their storage in a controlled temperature, heated, refrigerated, frozen or vitrified state.

Within certain embodiments, methods for increasing survival of sperm, oocyte, embryo, cells, tissues are provided that include contacting them with a composition of this invention. In yet other aspects, methods for preserving the function of sperm, eggs and cells, for reducing the loss of sperm-function (and egg, oocyte and cell-function) and sperm, egg, oocyte & cell damage are provided. In yet other aspects, methods for improving the function of sperm and cells are provided. Within related aspects, medium for storing sperm, oocyte, embryo or cells is provided. Within yet related aspects, medium and methods for sperm-banking, oocyte-banking, embryo-banking or cell-banking are provided. In another aspect, the water-based lubricant may also be used to coat tissues, surfaces and synthetic polymers, such as condoms. Within related aspects, novel condom designs are also provided.

Within certain embodiments, the novel water-based storage media compositions may be useful as compositions for collection of various biological samples, such as, without limit, cerebrospinal fluid, biopsy cells, biopsy tissue, cysts, tumors, saliva, stool, buccal swab, tissue, cells, fluid, blood, or a mixture thereof. Within certain related aspects, the compositions of this invention preserve viability of the collected biological material. Within certain other aspects, the compositions of this invention are useful as culturing or extending media immediately after collection of biological samples. Within certain other aspects, the compositions of this invention are useful as culturing or extending media immediately for biological samples following their storage in a refrigerated, frozen or vitrified state. Within certain other aspects, the compositions of this invention are useful as storage media for storage of biological samples in a controlled temperature, heated, refrigerated, frozen or vitrified state.

Within certain embodiments, the novel water-based storage media compositions may be useful as compositions for collection of various microbiological flora (such as, without limit, bacteria, fungi, virus etc) from biological samples, such as, without limit, cerebrospinal fluid, biopsy cells, biopsy tissue, cysts, tumors, saliva, stool, buccal swab, cells, tissue, fluid, blood or a mixture thereof. Within certain related aspects, the compositions of this invention preserve viability of the collected micro flora. Within certain other aspects, the compositions of this invention are useful as culturing or extending media of the micro flora immediately after collection of biological samples. Within certain other aspects, the compositions of this invention are useful as culturing or extending media of the micro flora immediately for biological samples following their storage in a refrigerated, frozen or vitrified state. Within certain other aspects, the compositions of this invention are useful as storage media for storage of micro flora in a controlled temperature, heated, refrigerated, frozen or vitrified state. Within certain aspects, the micro flora collected using the novel compositions are used in, without limit, development of assays, small molecules, therapeutics, high-throughput screenings etc.

Within certain aspects, the compositions and articles of this invention are generally prepared and/or produced by any method, including combining the active ingredients in the appropriate amounts and concentrations in a container and mixing. If need be, the mixtures are heated or cooled to aid in salvation of the ingredients. The compositions are preferably sterile and the most preferred method of sterilization is passing through a 0.2 micron filter. Within certain aspects, the compositions of this invention also have a high degree of clarity, preferably a turbidity of less than about 2, as measured with standard turbidimetric procedures known in the art.

Within certain embodiments, the novel water-based lubricant compositions may be useful as compositions for collection of various biological organs, such as, without limit, vagina, penus, kidney, lung, heart, liver, bone, skin and the like or a mixture thereof. Within certain related aspects, the compositions of this invention preserve viability of the collected organs. Within certain other related aspects, the compositions of this invention physiological function of the collected organs. For example, the compositions of this invention may enhance the function of an organ post-transplantation, by reducing the rejection rate. Within certain other aspects, the compositions of this invention are useful as culturing or extending media immediately after collection of organs. Within certain other aspects, the compositions of this invention are useful as culturing or extending media immediately for organs following their storage in a room temperature, heated, body temperature, refrigerated, frozen or vitrified state. Within certain other aspects, the compositions of this invention are useful as transportation solutions for organs. Within certain other aspects, the compositions of this invention are useful as transportation solutions for organs. Within certain other aspects, the compositions of this invention improve the viability and/or physiological function of organs during culture, during storage, transportation and during in vivo and in vitro use.

Within certain embodiments, the novel water-based lubricant compositions may be useful as compositions for use during medical treatments for, such as, without limit, wounds, rashes, burns, bruises, transplants and the like.

Within certain embodiments, the sample is obtained from animals, including human, bovine, canine, equine, porcine, ovine, avian, rodent or rare and exotic species or is artificially generated.

IV. Novel Condoms

A condom generally refers to a receptacle structured for collecting semen from a penis, as described in the U.S. Manual of Patent Classification 604/349. A condom is usually flexible and is shaped and designed so as to fit around the penis to receive emitted semen. It is generally shaped as a tube extending from an open end to a closed end, with an elongated portion in the middle. The condom has an inner and an outer surface.

Within certain embodiments, the present invention is directed towards novel articles, such as a novel condom, that may not capture all or most of sperm or semen during coitus. Within a preferred aspect, the novel condom may not prevent pregnancy. Within a further preferred aspect, the novel condom may aid in the process of pregnancy.

Within certain aspects, the condom may have one or more holes present in the closed end that would allow semen or sperm to escape during or post coitus. Within another related aspect, the condom may have one or more holes present in the elongated portion of the tube like structure that would allow semen or sperm to escape during or post coitus. Within certain other aspects, the condom of this invention may have holes present in the closed end and in the elongated middle portion.

Within certain aspects, the condom of this invention is lubricated. Within certain related aspects, the lubricant for the condom is non-spermicidal. Within certain further related aspects, the non-spermicidal lubricant composition is as described above in this invention.

Within certain aspects, the compositions and articles of this invention are generally prepared and/or produced by any method. Various methods of manufacturing condoms are well known in the art, such as, without limit, dip-casting (such as US 2005/0076917 and the references cited therein). Within some aspects, the condom is manufactured and sold in a rolled configuration. Within some other aspects, a condom is typically made of thin, flexible, natural or synthetic elastic material, such as, without limit, latex, rubber or rubber-like material. Condoms are generally packaged individually, with or without a lubricant agent, in a sealed pouch. Within certain aspects, the holes are created in the novel condoms during the process of manufacturing. Examples of various manufacturing process steps, without limit, are dusting of condoms, rolling around thickened ring at the open end of the condom that leaves the generally closed end forming a cup within the circumference of the ring. Within certain other aspects, the holes are created in the novel condoms after the manufacturing of condom is complete. Within certain yet other aspects, the holes are created in the novel condoms prior to their use.

The following examples are offered by way of illustration, and not by way of limitation.

EXAMPLES

Example 1

Compositions related to this invention are prepared by the following procedure. First, a balanced salt solution comprising of phosphate buffered saline (PBS) was prepared using the following ingredients:

| | |
|---|---|
| Na2HPO4 (anhydrous) | approx. 1.09 g |
| NaH2PO4 (anhydrous) | approx. 0.32 g |
| NaCl | approx. 9 g |
| Mix in distilled water to dissolve and adjust pH to 8.0. | |
| Add distilled water to bring the final volume to | approx. 1000 mL |

Viability maintaining agents in the form of divalent ions were added to the PBS solution. Two agents were used in this instance: calcium ions and magnesium ions. Both were added to the PBS solution to achieve a final concentration of approx. 1 mM in each.

A base lubricant, hydroxypropyl methyl cellulose (hypromellose) was added in the following amounts and the resultant mixtures were gently mixed to obtain a solution for each composition:

Novel composition 1=0.5% (w/v) hypromellose
Novel composition 2=0.75% w/v) hypromellose Example 2

Flow cytometric (FCM) analysis of sperm viability: The protocol for measuring the number of dead spermatozoa was according to published literature (24). Briefly, thawed spermatozoa were adjusted to a concentration of $1.0 \times 10^6$ spermatozoa/ml in phosphate buffered saline (PBS) and washed by centrifugation. Washed spermatozoa were incubated with 3 ml of various lubricant compositions, including KY lubricant, Pre-Seed Lubricant (Bio-Origyn, LLC), and compositions of this invention, including Novel Composition 1, Novel Composition 2 and other lubricants (not shown) for 20 minutes (from Example 1). Afterwards, the spermatozoa were washed once, resuspended in PBS and incubated with annexinV-fluorescein isothiocyanate (FITC) solution (Pharmingen, San Diego, Calif.) and propidium iodide (PI) (Pharmingen, San Diego, Calif.) in the dark. The spermatozoa were washed once and the level of sperm viability was analyzed by four-color FCM analysis on a FACSort (Becton Dickinson, Mountain View, Calif.). The sperm population was gated using forward-angle light scatter to exclude debris and aggregates. A minimum of 10,000 individual spermatozoa were examined in each assay at a flow rate of <100 cells/s. The excitation wavelength was 488 nm supplied by an argon laser at 250 mW. Green (FITC-derived) fluorescence was measured using a 530 nm filter and the red fluorescence (PI) with a 610 nm filter. The percentage of PI positive cells (dead spermatozoa) were calculated using FACSCaliber program (Becton Dickinson, Mountain View, Calif.) and the relative number of dead spermatozoa determined with each lubricant composition was calculated, with the percentage of dead spermatozoa determined using K-Y Jelly arbitrarily assigned a value of 100%. Results are presented in Table I.

REFERENCES CITED

U.S. Patent Documents
U.S. Pat. No. 3,965,906
U.S. Pat. No. 4,128,631
U.S. Pat. No. 4,184,974
U.S. Pat. No. 4,267,268
U.S. Pat. No. 4,670,256
U.S. Pat. No. 4,883,658
U.S. Pat. No. 4,981,686
U.S. Pat. No. 5,015,474
U.S. Pat. No. 5,128,132
U.S. Pat. No. 5,342,617
U.S. Pat. No. 5,800,807
U.S. Pat. No. 5,885,591
U.S. Pat. No. 6,139,848
U.S. Pat. No. 6,140,121
U.S. Pat. No. 6,428,791
U.S. Pat. No. 6,593,309
U.S. Pat. No. 6,610,331
U.S. Pat. No. 6,861,079
U.S. Pat. No. 6,864,046
US 2002/0193350
US 2003/0224070
US 2004/0073964
US 2005/0076917
Foreign Patent Documents
EP0888 117
Other References
1. S. Greaves and C. Wang. A fertile field. Nat Cell Biol. 2002 Oct.; 4 Suppl:S2
2. A. Glasier. Contraception—Past and future. Nat Cell Biol. 2002 Oct.; 4 Suppl:S3-S6
3. P. M. Wassarman. Channels of communication in the ovary. Nat Cell Biol. 2002 Oct.; 4 Suppl:S7-S9
4. L. R. Fraser ART: Boon or bane? Nat Cell Biol. 2002 Oct.; 4 Suppl:S11-S13
5. R. M. L. Winston and K. Hardy. Are we ignoring potential dangers of in vitro fertilization and related treatments? Nat Cell Biol. 2002 Oct.; 4 Suppl:S14-S18
6. G. P. Schatten. Safeguarding ART. Nat Cell Biol. 2002 Oct.; 4 Suppl:S19-S22
7. R. A. Charo, J. D. Children by choice: reproductive technologies and the boundaries of personal autonomy. Nat Cell Biol. 2002 Oct.; 4 Suppl:S23-S28
8. P. Katz, R. Nachtigall and J. Showstack. The economic impact of the assisted reproductive technologies. Nat Cell Biol. 2002 Oct.; 4 Suppl:S29-S32
9. R. M. Sharpe and S. Franks. Environment, lifestyle and infertility—an inter-generational issue. Nat Cell Biol. 2002 Oct.; 4 Suppl:S33-S40
10. M. M. Matzuk and D. J. Lamb Genetic dissection of mammalian fertility pathways. Nat Cell Biol. 2002 Oct.; 4 Suppl:S41-S49
11. M. D. Champion and R. S. Hawley. Playing for half the deck: the molecular biology of meiosis. Nat Cell Biol. 2002 Oct.; 4 Suppl:S50-S56
12. J. P. Evans and H. M. Florman. The state of the union: the cell biology of fertilization. Nat Cell Biol. 2002 Oct.; 4 Suppl:S57-S63
13. Butler D. The fertility riddle. Nature. 2004 Nov. 4; 432 (7013):38-9.
14. Powell K. Skeptics demand duplication of controversial fertility claim. Nat Med. 2005 Sep.; 11(9):911.
15. Kirichok Y, Navarro B, Clapham D E. Whole-cell patch-clamp measurements of spermatozoa reveal an alkaline-activated Ca2+ channel. Nature. 2006, 9; 439(7077):737.
16. Powell K. Fertility treatments: Seeds of doubt. Nature. 2003 Apr. 17; 422(6933):656-8.
17. Chen Y, Cann M J, Litvin T N, Iourgenko V, Sinclair M L, Levin L R, Buck J. Soluble adenylyl cyclase as an evolutionarily conserved bicarbonate sensor. Science. 2000 Jul. 28; 289(5479):625-8.
18. Goldenberg R L, White R. The effect of vaginal lubricants on sperm motility in vitro. Fertil Steril. 1975 Sep.; 26(9): 872-3.
19. Kutteh W H, Chao C H, Ritter J O, Byrd W. Vaginal lubricants for the infertile couple: effect on sperm activity. Int J Fertil Menopausal Stud. 1996 Jul.-Aug.; 41(4):400-4.
20. Frishman G N, Luciano A A, Maier D B. Evaluation of Astroglide, a new vaginal lubricant: effects of length of exposure and concentration on sperm motility. Fertil Steril. 1992 Sep.; 58(3):630-2.
21. Anderson L, Lewis S E, McClure N. The effects of coital lubricants on sperm motility in vitro. Hum Reprod. 1998 Dec.; 13(12):3351-6.
22. Tagatz G E, Okagaki T, Sciarra JJ. The effect of vaginal lubricants on sperm motility and viability in vitro. Am J Obstet Gynecol. 1972 May 1; 113 (1):88-90.
23. Visconti et al., Novel signaling pathways involved in sperm acquisition of fertilizing capacity, Journal of Reproductive Immunology, 2002, 53,133-150.
24. Glander H J, Schaller J. Binding of annexin V to plasma membranes of human spermatozoa: a rapid assay for detection of membrane changes after cryostorage. Mol Hum Reprod. 1999 Feb.; 5(2):109-15.

We claim:

1. A composition comprising:
    (a) an aqueous lubricant base comprising a combination of lubricious agents in an aqueous balanced salt solution wherein the combination comprises methylparaben, glycerol, and a cellulose selected from the group consisting of methylcellulose, hydroxymethyl cellulose, hydroxyethyl cellulose, and hydroxypropylmethyl cellulose;
    (b) a combination of chloride salts of calcium, sodium, potassium, and magnesium ions; and
    (c) vitamin E;
    wherein the composition excludes additional therapeutic drugs, has a pH in the range of 5.0-9.0, has an osmolality in the range of 200 to 700 mOsm/kg, and kills less than about 1% of the spermatozoa that are exposed to the composition.

2. The composition of claim 1, wherein the cellulose is hydroxypropylmethyl cellulose.

3. The composition of claim 1, wherein the pH is in the range of 7.0 to 8.5.

4. The composition of claim 1, wherein the composition is devoid of EDTA.

5. The composition of claim 1, wherein the composition is formulated as a solution, gel, foam, or cream.

6. The composition of claim 1, wherein the osmolality of the composition is between 250 and 500 mOsm/kg.

7. The composition of claim 6, wherein the osmolality of the composition is between 300 and 400 mOsm/kg.

8. The composition of claim 1, wherein the composition is contained within a single dose container.

9. A composition consisting of:
    (a) an aqueous lubricant base consisting of methylparaben, glycerol, and hydroxypropylmethyl cellulose in an aqueous balanced salt solution of dibasic sodium phosphate and monobasic sodium phosphate;
    (b) a combination of salts consisting of chloride salts of calcium, sodium, potassium, and magnesium; and
    (c) vitamin E
    wherein the composition has a pH in the range of 7.0-8.5 and an osmolality in the range of 200 to 700 mOsm/kg.

10. A composition comprising:
(a) an aqueous lubricant base comprising a combination of lubricious agents in an aqueous balanced salt solution wherein the combination comprises methylparaben, glycerol, and a cellulose selected from the group consisting of methylcellulose, hydroxymethyl cellulose, hydroxyethyl cellulose, and hydroxypropylmethyl cellulose;
(b) a combination of chloride salts of calcium, sodium, potassium, and magnesium ions; and
(c) an antioxidant;
wherein the composition excludes additional therapeutic drugs, has a pH in the range of 7.0-9.0, has an osmolality in the range of 200 to 700 mOsm/kg, and kills less than about 1% of the spermatozoa that are exposed to the composition.

11. The composition of claim 10 wherein the pH is in the range of 7.0 to 8.5.

12. The composition of claim 10, wherein the antioxidant is vitamin E.

* * * * *